(12) United States Patent
Hertel

(10) Patent No.: US 9,802,381 B2
(45) Date of Patent: Oct. 31, 2017

(54) CLOSURE ELEMENT FOR AN ABDOMINAL BELT

(71) Applicant: BAUERFEIND AG, Zeulenroda-Triebes (DE)

(72) Inventor: Stefanie Hertel, Plauen (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 0 days.

(21) Appl. No.: 14/396,826

(22) PCT Filed: Apr. 26, 2013

(86) PCT No.: PCT/EP2013/058716
§ 371 (c)(1),
(2) Date: Oct. 24, 2014

(87) PCT Pub. No.: WO2013/160444
PCT Pub. Date: Oct. 31, 2013

(65) Prior Publication Data
US 2015/0104619 A1    Apr. 16, 2015

(30) Foreign Application Priority Data
Apr. 27, 2012   (DE) .......................... 10 2012 009 250

(51) Int. Cl.
*B32B 3/02* (2006.01)
*A44B 18/00* (2006.01)
*A61F 5/01* (2006.01)

(52) U.S. Cl.
CPC ............... *B32B 3/02* (2013.01); *A44B 18/00* (2013.01); *A61F 5/01* (2013.01); *B32B 2250/03* (2013.01); *B32B 2435/00* (2013.01); *B32B 2535/00* (2013.01); *Y10T 24/27* (2015.01); *Y10T 24/36* (2015.01); *Y10T 24/45257* (2015.01); *Y10T 428/24777* (2015.01)

(58) Field of Classification Search
None
See application file for complete search history.

(56) References Cited

U.S. PATENT DOCUMENTS 2,527,205 A    10/1950   Zaras
4,869,724 A *   9/1989   Scripps .......................... 604/389
(Continued)

FOREIGN PATENT DOCUMENTS

AU          622098 B3    2/1992
DE        19725648 C1    8/1998
(Continued)

OTHER PUBLICATIONS

International Search Report for PCT/EP2013/058716, ISA/EP, dated Jul. 22, 2013.
(Continued)

*Primary Examiner* — Laura Powers
(74) *Attorney, Agent, or Firm* — Stephen T. Olson; Harness, Dickey & Pierce, P.L.C.

(57) ABSTRACT

A flexible closure element for a closure of a medical or orthopedic product or sports product includes a first and second elastic cover layer and a sheet-type stabilizing element therebetween. The sheet-type stabilizing element is slotted over a least half of a length of the stabilizing element on at least one of two longitudinally running edges.

22 Claims, 4 Drawing Sheets

(56) References Cited

U.S. PATENT DOCUMENTS

Figure 1:
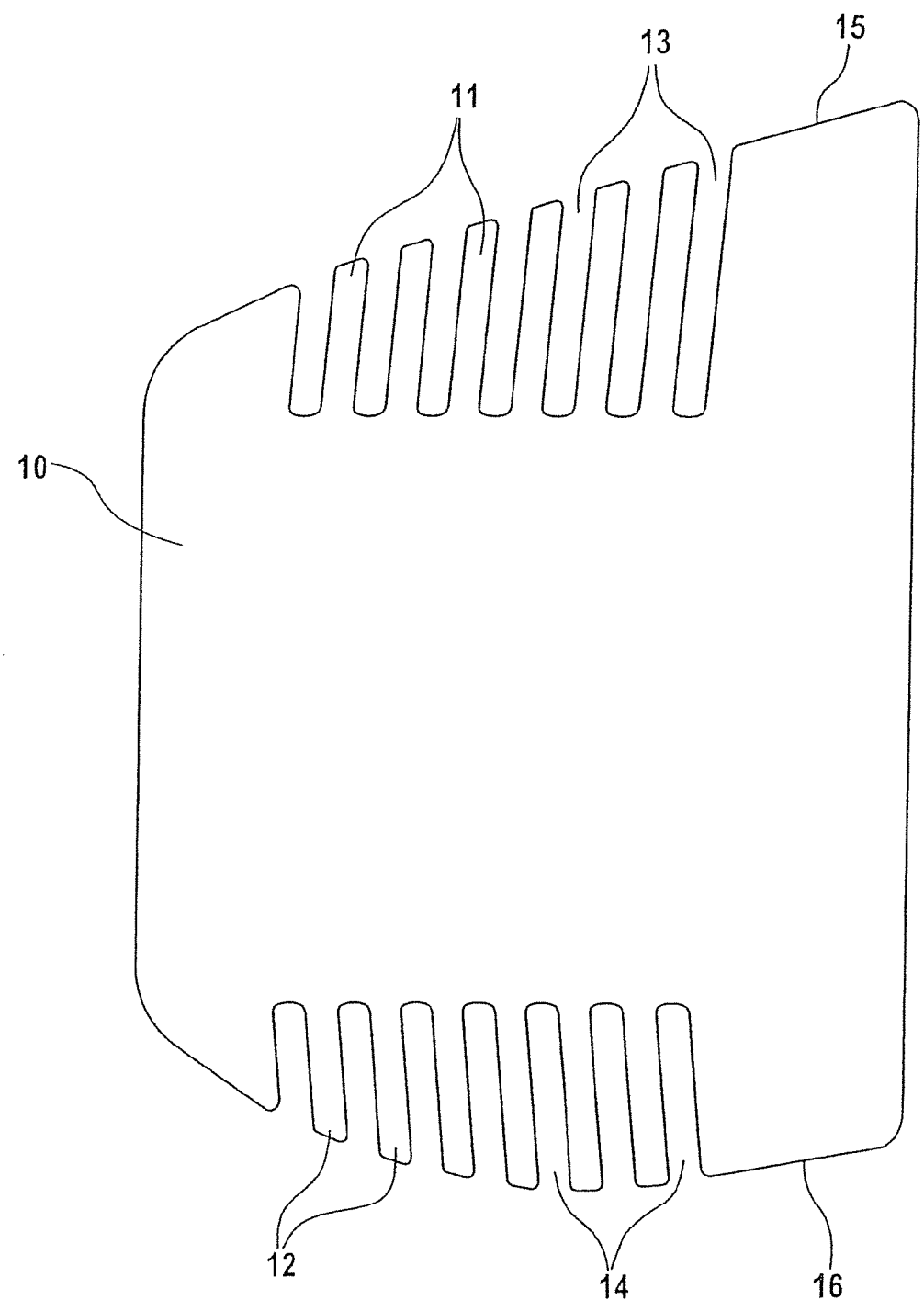

| | | | |
|---|---|---|---|
| 4,950,282 A * | 8/1990 | Beisang et al. | 606/216 |
| 5,362,304 A | 11/1994 | Varn | |
| 6,024,712 A | 2/2000 | Iglesias et al. | |
| 6,478,759 B1 | 11/2002 | Modglin et al. | |
| 7,815,585 B2 | 10/2010 | Vollbrecht | |
| 2003/0199799 A1 | 10/2003 | Modglin et al. | |
| 2008/0021428 A1 * | 1/2008 | Klofta et al. | 604/385.01 |
| 2009/0036013 A1 * | 2/2009 | Poulakis | 442/301 |
| 2011/0295268 A1 | 12/2011 | Hendricks | |

FOREIGN PATENT DOCUMENTS

| | | |
|---|---|---|
| DE | 202004001381 U1 | 6/2004 |
| DE | 102005031867 A1 | 1/2007 |
| FR | 1050235 A | 1/1954 |
| WO | WO-01/66051 A2 | 9/2001 |

OTHER PUBLICATIONS

International Preliminary Report on Patentability with annexes for PCT/EP2013/058716, IPEA/EP, Munich, dated Aug. 7, 2014.
English Translation of the International Preliminary Report on Patentability regarding International Application No. PCT/EP2013/058716.
Chinese Office Action issued in the parallel procedure for Chinese Patent Application 201380022234.X, dated Jun. 3, 2015, with English translation thereof.

* cited by examiner

CLOSURE ELEMENT FOR AN ABDOMINAL BELT

CROSS-REFERENCE TO RELATED APPLICATIONS

This application is a 371 U.S. National Stage of International Application No. PCT/EP2013/058716, filed Apr. 26, 2013. This application claims the benefit of German Patent Application No. DE 10 2012 009 250.4, filed Apr. 27, 2012. The entire disclosures of the above applications are incorporated by reference herein.

The invention relates to flexible closure element, for example, an abdominal closure element for bandages and orthotics as well as closures and products, for example, abdominal closures of bandages and orthotics comprising such closure elements.

Closures comprised of two closure elements, for example, Velcro-type hook-and-loop closures are known. These closures may have a certain width, depending on the field of use. This is true of abdominal closures, for example. This width can make the closures inflexible in an undesirable manner.

Abdominal closures comprised of abdominal closure elements for bandages and orthotics are known from DE 10 2005 031 867 A1, for example. These are often embodied as Velcro closures.

Such abdominal closures must have a certain width in order to ensure a secure hold. They are also difficult to bend for this secure hold. When the orthotic or the bandage is worn, the abdominal closure thus purses unpleasantly into the patient's body, in particular into the abdomen when sitting or when bending the upper body forward. Thus with existing abdominal closures of bandages and orthotics, there is the disadvantage that in particular with many patients the upper edge of the closure presses into the abdomen or against the costal arch and the lower edge of the closure presses into the inguinal region.

The object of the invention is to provide closures, in particular abdominal closures, which will overcome the disadvantages of the prior art, in particular permitting a secure hold of a bandage or orthotics, for example, while nevertheless being comfortable to wear, in particular during movements and in positions of the body, in particular the upper body, such as bending forward, sitting or turning.

The technical problem on which the present invention is based is solved by providing a flexible closure element according to claim 1.

The technical problem on which the invention is based is solved by providing a flexible closure element in particular, wherein the closure element has two elastic cover layers, a sheet-type stabilizing element being provided between the two elastic cover layers, such that the sheet-type stabilizing element has at least one slot.

In one preferred embodiment, the closure element is an abdominal closure element. However the closure element may also be used for other types of closures, in particular for closures having a certain width, for example, similar to an abdominal closure. These are preferably closure elements of closures on medical and orthopedic products or sports products, such as orthotics or bandages, in particular torso bandages, torso orthotics, back bandages, back orthotics, shoulder bandages, shoulder orthotics, arm bandages, arm orthotics, joint bandages, joint orthotics, knee bandages or knee orthotics.

For example, the closure elements according to the invention are suitable not only for abdominal closures on abdominal belts but also for closures on shoulder belts, in particular wide shoulder belts. Here again the flexibility created by the slots can increase wearing comfort, for example, in shoulder movements and turning movements of the upper body.

In one preferred embodiment, the sheet-type stabilizing element is slotted on at least one of the two longitudinal edges over at least one-half of the length of the stabilizing element. In one preferred embodiment, the upper edge and the lower edge of the sheet-type stabilizing element are slotted. In one preferred embodiment, the two elastic cover layers are made of a textile material and the sheet-type stabilizing element is made of a plastic. In one preferred embodiment, the sheet-type stabilizing element has slots on at least one of the two longitudinal edges, these slots being at least one-half as wide as the webs between the slots. In one preferred embodiment, the sheet-type stabilizing element has slots on at least one of the two longitudinal edges and has webs between the slots, such that the length of the slots and the webs corresponds to at least one-tenth of the height of the stabilizing element. In one preferred embodiment, the sheet-type stabilizing element is welded, glued or sewn to the two elastic cover layers. In one preferred embodiment, the closure element can be connected flexibly to a belt or a bandage or an orthotic by means of a Velcro-type closure. In one preferred embodiment, the closure element has an attached pocket.

The invention also relates to a closure consisting of two closure elements according to the invention. The closure is preferably an abdominal closure. The closure may be a Velcro closure, a hook closure, a button closure or a snap closure, for example.

The invention also relates to a product, for example, a belt, a bandage or an orthotic, comprising at least one closure according to the invention or one closure element according to the invention.

The flexible closure element according to the invention may be an abdominal closure element in particular. However, the alternative and preferred embodiments of an abdominal closure element according to the invention, as mentioned below, are also to be understood as alternative and preferred embodiments of a flexible closure element according to the invention, which is not an abdominal closure element.

The technical problem on which the invention is based is thus solved in particular by providing an abdominal closure element, wherein the abdominal closure element has at least two elastic cover layers with a sheet-type stabilizing element provided between the two elastic cover layers, and the sheet-type stabilizing element has at least one slot.

In one preferred embodiment, the abdominal closure element has at least two elastic cover layers, with a sheet-type stabilizing element provided between the two elastic cover layers, the sheet-type stabilizing element being slotted on at least one of the two longitudinal edges over at least one-half of the length of the stabilizing element.

According to the invention, the sheet-type stabilizing element thus has at least one slot. A plurality of slots is preferred.

The at least one slot may be located in the internal region or in the external region of the sheet-type stabilizing element. The at least one slot may thus end at an edge of the sheet-type stabilizing element. However, it may also be completely surrounded by the sheet-type stabilizing element. With at least two slots, in particular a plurality of slots, some slots may be situated on an edge of the sheet-type stabilizing element while other slots may be surrounded entirely by the stabilizing element.

The slots may run in any direction, for example, longitudinally to the sheet-type stabilizing element or transversely to the sheet-type stabilizing element. The slots may also be shaped like a cross formed by two intersecting slots, for example. The slots may have a length of at least 1 cm, for example, and at most 20 cm. The slots may have a width of at least 0 cm and at most 2 cm, for example. A width of 0 cm is achieved when a slot is merely cut into the sheet-type stabilizing element but no material is cut out of the sheet-type stabilizing element.

In one preferred embodiment, the abdominal closure element is flexible.

In one preferred embodiment, the abdominal closure element is suitable for bandages and orthotics.

It has surprisingly been found that a design of an abdominal closure element comprised of two elastic cover layers and a sheet-type stabilizing element which is slotted, in particular being slotted on at least one of the two longitudinal edges and placed in between the two cover layers offers a good and secure hold, for example, of a bandage or orthotic and absorbs well the radial tensile forces that occur, in particular due to the sheet-type stabilizing element which imparts a large area stability to the abdominal closure element, but nevertheless permits convenient and pleasant use, even when the upper body is bent or when sitting, due to the slots in the sheet-type stabilizing element. A comfortable elastic zone is created due to the special design including slots, preferably in the edge region of the abdominal closure element, permitting a better fit to the various body shapes. In addition the elastic boundary zones of the abdominal closure element allow unrestricted abdominal breathing.

It is thus preferable that on the upper and/or lower edges, the sheet-type stabilizing element is provided with slots or meandering or groove-type recesses, which yield partially elastic bordering regions having the desired properties described here in cooperation with the elastic cover layers.

In one preferred embodiment, the upper edge and/or the lower edge of the sheet-type stabilizing element is/are slotted over at least one-half of the edge length. In one preferred embodiment, the upper edge and/or the lower edge of the sheet-type stabilizing element is/are slotted over at least three-fourths of the edge length.

In one preferred embodiment, the upper edge and the lower edge of the sheet-type stabilizing element are slotted over at least one-half of the edge length. In one preferred embodiment, the upper edge and the lower edge of the sheet-type stabilizing element are slotted over at least three-fourths of the edge length.

In one preferred embodiment, the upper edge and the lower edge of the sheet-type stabilizing element are slotted.

In one preferred embodiment, the two elastic cover layers are made of or contain a textile material. The textile material may be in particular a flat textile material, for example, a velour, a woven or knit fabric. In one preferred embodiment, the sheet-type stabilizing element is made of or contains a plastic. Those skilled in the art may readily select suitable plastics of a suitable hardness and strength.

In one preferred embodiment, the two elastic cover layers are made of a textile material and the sheet-type stabilizing element is made of a plastic.

In one preferred embodiment, the sheet-type stabilizing element has slots on at least one of the two longitudinal edges, where these slots are at least one-half as wide as the webs formed between the slots. The width of the slots is preferably at least 0.1 cm and at most 2 cm, in particular approx. at least 0.2 cm and at most 1 cm.

In one preferred embodiment, the sheet-type stabilizing element has slots on at least one of the two longitudinal edges and has webs between the slots, such that the length of the slots and the webs corresponds to at least one-tenth of the height of the stabilizing element. The length of the slots is preferably at least 1 cm and at most 10 cm, in particular approx. at least 2 cm and at most 6 cm.

In one preferred embodiment, the sheet-type stabilizing element is welded, glued or sewn to the two elastic cover layers. However, the sheet-type stabilizing element may also be simply inserted between the two elastic cover layers such that preferably the two elastic cover layers are welded, glued or sewn together at their edges.

In one preferred embodiment, the abdominal closure element is flexibly connectable to an abdominal belt or a bandage or an orthotic by a Velcro-type closure. In one preferred embodiment, the Velcro-type closure is a hook-and-loop closure.

In one preferred embodiment, at least one of the two elastic cover layers has a hook-and-loop surface on its outside.

In one preferred embodiment, the abdominal closure element has an attached pocket. This is suitable preferably for insertion of a hand, so that the abdominal closure element can be pulled well and can be connected to a second abdominal closure element. The pocket is therefore preferably an insertion pocket adapted to the shape of a hand.

The present invention also relates to an abdominal closure consisting of at least one abdominal closure element according to the invention, preferably two abdominal closure elements according to the invention.

In one preferred embodiment, the abdominal closure is a Velcro closure, a hook closure, a button closure or a snap closure. The abdominal closure is especially preferably a Velcro closure.

The present invention also relates to a bandage or an orthotic comprising at least one abdominal closure element according to the invention, preferably two abdominal closure elements according to the invention, or one abdominal closure according to the invention.

The orthotic is preferably a torso orthotic or a back orthotic.

Preferred embodiments are also derived from the dependent claims.

The invention is explained in greater detail below on the basis of the exemplary embodiment illustrated in the drawings, without restricting the invention in any way.

Figure 2:
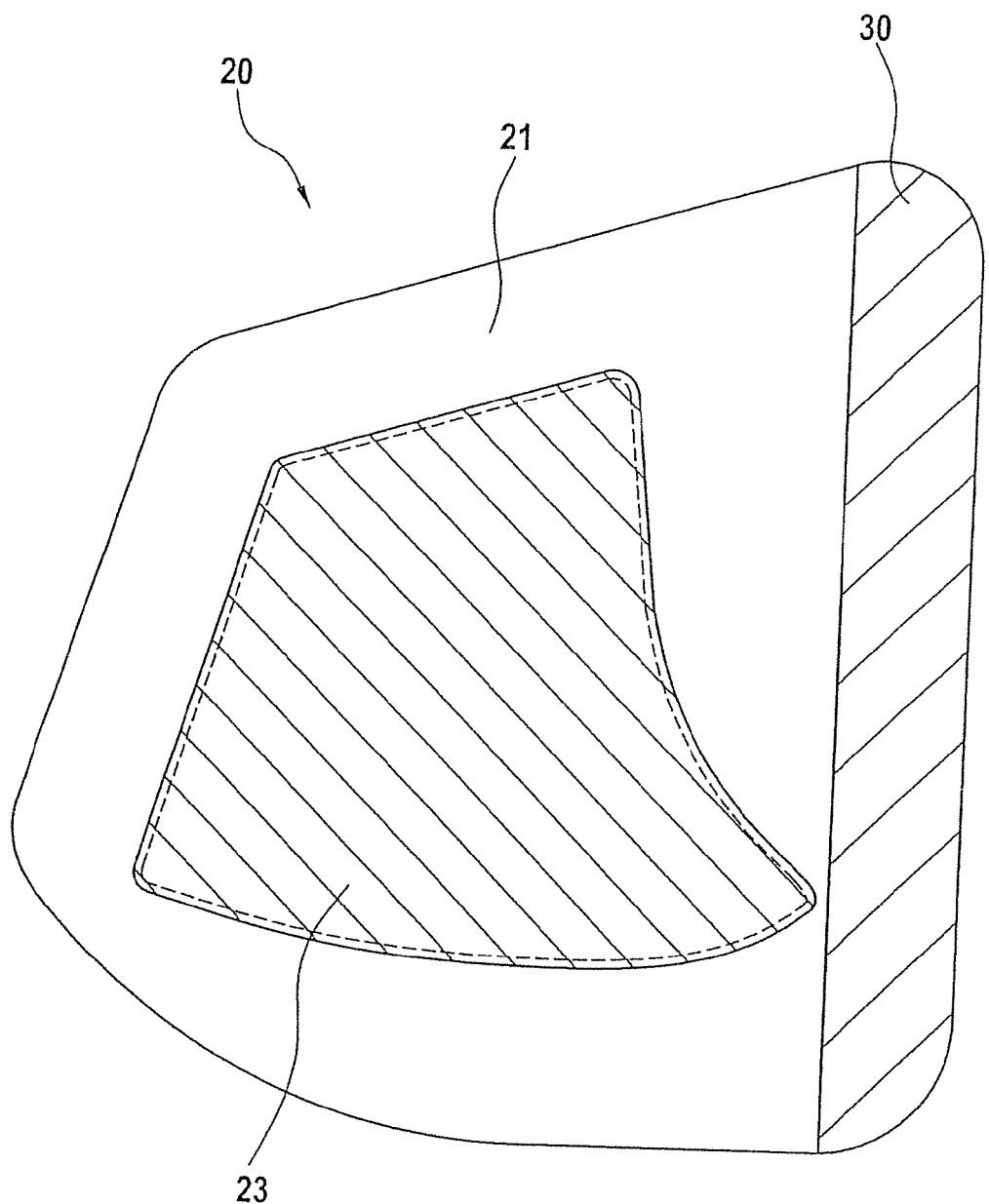
Figure 3:
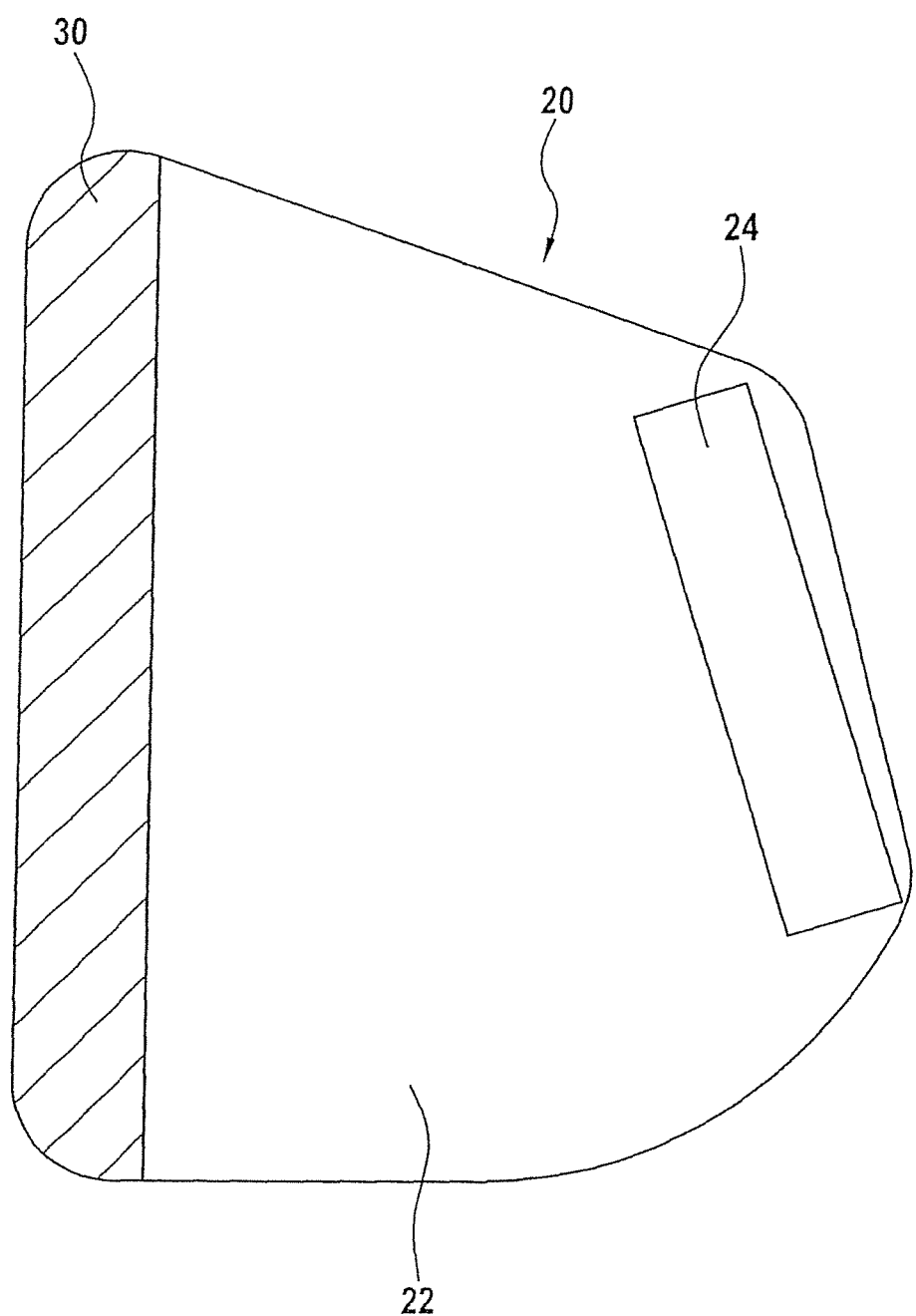
Figure 4:
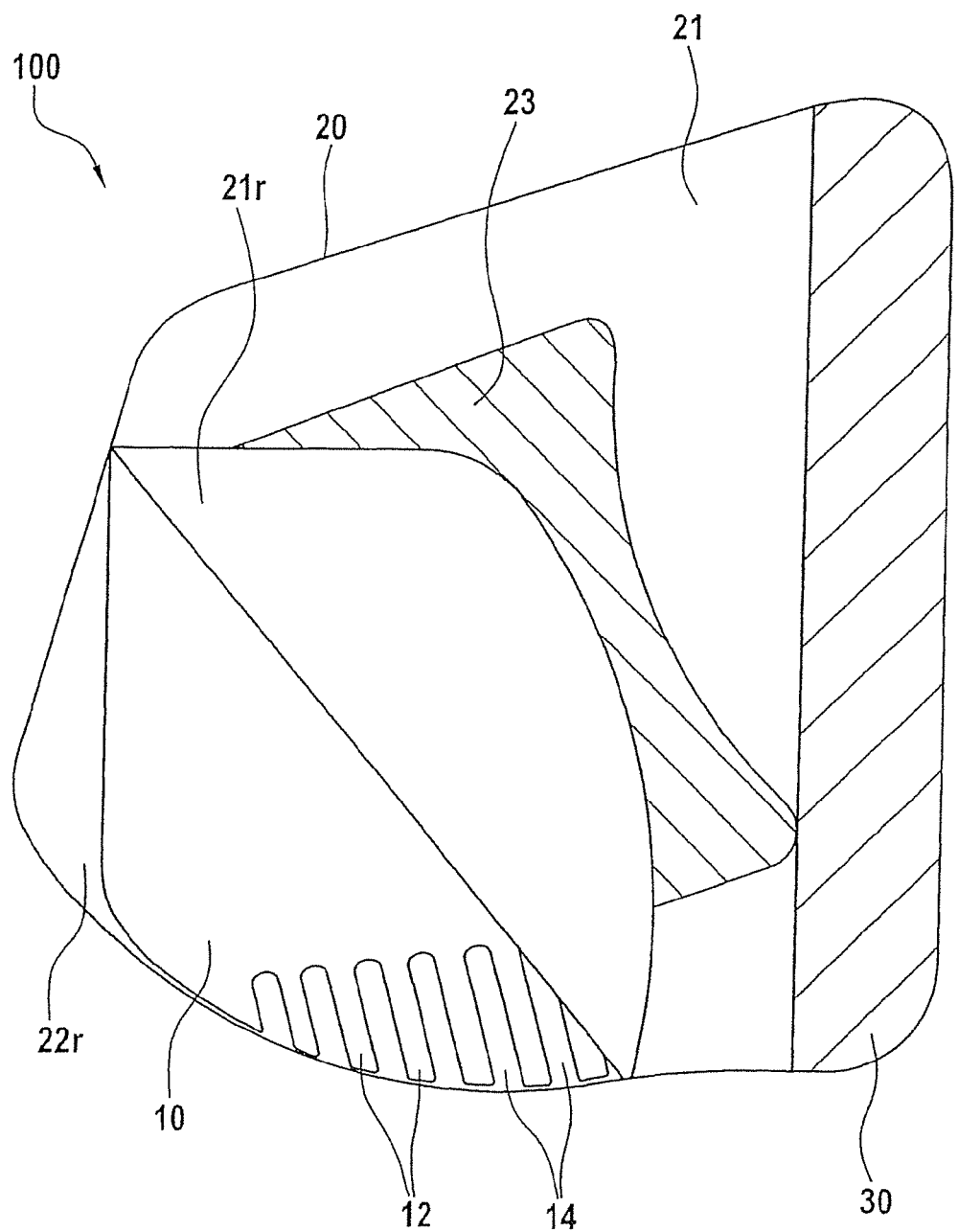

The figures show:

FIG. 1: A top view of a sheet-type stabilizing element having slots of an abdominal closure element according to the invention;

FIG. 2: A top view of the first elastic cover layer of an abdominal closure element according to the invention;

FIG. 3: A top view of the second elastic cover layer of an abdominal closure element according to the invention;

FIG. 4: Top view of an abdominal closure element according to the invention, in which one of the two elastic cover layers is partially folded open.

EXAMPLE

FIG. 1 shows a sheet-type stabilizing element (10) having slots or recesses (13) on the upper edge (15) of the stabilizing element (10) and having slots or recesses (14) on the lower edge (16) of the stabilizing element (10). Between the slots (13, 14) the stabilizing element (10) has webs (11, 12). The stabilizing element (10) is made of a plastic molded in one piece.

FIG. 2 shows a view of the first elastic cover layer (21) of an abdominal closure element according to the invention. The first cover layer (21) together with a second cover layer, to which it has been sewn or glued, for example, at the edge, forms a sheathing or casing (20) for a sheet-type stabilizing element. A pocket (23) is attached, for example, by sewing or gluing, to the first elastic cover layer (21) and is suitable for engagement with a hand. One end of the cover layer (21) is designed as a Velcro opening closure (30) with which the abdominal closure can be applied to a belt or an orthotic.

FIG. 3 shows a top view of the second elastic cover layer (22) of an abdominal closure element according to the invention. The second cover layer (22) together with the first cover layer from FIG. 2, to which it is sewn or glued at the edge, for example, forms a sheathing or casing (20) for a sheet-type stabilizing element. A Velcro closure (24) is attached to the second elastic cover layer (21), for example, by sewing or gluing, with which the abdominal closure element can be connected to a second abdominal closure element which also has a Velcro closure to form an abdominal closure. One end of the cover layer (22) is designed as a Velcro opening closure (30) with which the abdominal closure can be applied to a belt or to an orthotic.

FIG. 4 shows an abdominal closure element (100) according to the invention, having the first elastic cover layer (21) from FIG. 2, the second elastic cover layer (22) from FIG. 3 and the sheet-type stabilizing element (10) from FIG. 1. Each elastic cover layer (21, 22) comprises a flat textile material.

The first elastic cover layer (21) is partially folded over to allow a view of the sheet-type stabilizing element (10) provided between the two elastic cover layers (21, 22). Thus the insides (21r, 22r) of the two cover layers can also be seen. Normally the sheet-type stabilizing element (10) and the insides (21r, 22r) are not visible because the two elastic cover layers (21, 22) are joined to one another peripherally at least on their edges, for example, by gluing or sewing.

Due to the special design with slots (14) and webs (12) in the lower edge region and with slots in the upper edge region (not visible) of the stabilizing element (10) of the stabilizing element (10), a comfortable elastic zone is created, permitting a better fit to the various body shapes. In addition, the resulting elastic edge zones of the abdominal closure element (100) allow unrestricted abdominal breathing.

The first elastic cover layer (21) has on the outside an attached insertion pocket (23) adapted to the shape of the hand. It is suitable for inserting a hand, so that the abdominal closure element can be wrapped well when applying a bandage or an orthotic and can also be attached to a second abdominal closure element.

At one end of the abdominal closure element (100), there is a partial piece (30) which opens like a mouth and has interior hook-and-loop surfaces. This piece (30) makes it possible to attach the abdominal closure element (100) to a belt, to a bandage or to an orthotic and to release it again as needed.

The invention claimed is:

1. An orthotic comprising:
   at least one abdominal closure including two flexible closure elements, each of the flexible closure elements including:
   first and second elastic cover layers; and
   a sheet-type stabilizing element for stabilizing the abdominal closure element, the sheet-type stabilizing element located between the first and second elastic cover layers, the sheet-type stabilizing element having first and second longitudinally running edges, wherein the sheet-type stabilizing element is slotted over at least half of a length of the stabilizing element on both of the first and second longitudinal running edges.

2. The orthotic according to claim 1, wherein the first and second elastic cover layers are made of a textile material, and the sheet-type stabilizing element is made of a plastic.

3. The orthotic according to claim 1, wherein the sheet-type stabilizing element is welded, glued or sewn to the two elastic cover layers.

4. The orthotic according to claim 1, wherein the closure element has a pocket attached to the first elastic cover layer, wherein the pocket is suitable for engagement with a hand.

5. The orthotic according to claim 1, wherein the closure is selected from a group consisting of a hook and loop type closure, a hook closure, a button closure and a snap closure.

6. The orthotic according to claim 1, wherein the first longitudinally running edge includes a first plurality of laterally extending slots and a second longitudinally running edge includes a second plurality of laterally extending slots, the first and the second pluralities of laterally extending slots being laterally spaced from one another to define a central, unslotted area.

7. The orthotic according to claim 6, wherein the central area has a lateral width greater than a length of any slot.

8. The orthotic according to claim 6, wherein the laterally extending slots of first and second pluralities of laterally extending slots extend to a perimeter shared by the first and second elastic cover layers.

9. The orthotic according to claim 1, wherein the first longitudinally running edge is linear and the second longitudinally running edge is arcuate.

10. The orthotic according to claim 1, wherein a length of slots along the first longitudinally running edge increase in a direction extending from a first end to a second end of the sheet stabilizing element.

11. An orthotic comprising:
   at least one abdominal closure including two flexible closure elements, each of the flexible closure elements including:
   first and second elastic cover layers; and
   a sheet-type stabilizing element for stabilizing the abdominal closure element, the sheet-type stabilizing element located between the first and second elastic cover layers, the sheet-type stabilizing element having first and second longitudinally running edges extending between a first end and a second end, at least one of the first and second longitudinally running edges being arcuate, both of the first and second longitudinally running edges slotted over at least half a respective first and second length.

12. The orthotic according to claim 11, wherein the first longitudinally running edge is linear and the second longitudinally running edge is arcuate.

13. The orthotic according to claim 1, wherein the sheet type stabilizing element is a one-piece plastic molded element.

14. The orthotic according to claim 1, wherein the first and second elastic cover layers are made of textile material.

15. The orthotic according to claim 1, wherein the sheet type stabilizing element is a one-piece plastic molded element and the first and second elastic cover layers are made of textile material.

16. The orthotic according to claim 1, wherein the two flexible closure elements are flexibly connectable to the orthotic by a hook-and-loop closure.

17. The orthotic according to claim 1, wherein the two flexible closure elements completely cover first and second sides of the sheet-type stabilizing element, respectively.

18. The orthotic according to claim 11, wherein the sheet type stabilizing element is a one-piece plastic molded element.

19. The orthotic according to claim 11, wherein the first and second elastic cover layers are made of textile material.

20. The orthotic according to claim 11, wherein the sheet type stabilizing element is a one-piece plastic molded element and the first and second elastic cover layers are made of textile material.

21. The orthotic according to claim 11, wherein the two flexible closure elements are flexibly connectable to the orthotic by a hook-and-loop closure.

22. The orthotic according to claim 11, wherein the two flexible closure elements completely cover first and second sides of the sheet-type stabilizing element, respectively.

\* \* \* \* \*